United States Patent [19]

Hamada et al.

[11] 4,154,744

[45] May 15, 1979

[54] PROCESS FOR PRODUCING A FURAN DERIVATIVE

[75] Inventors: Kazuhiko Hamada; Gohu Suzukamo, both of Ibaraki; Tsuneyuki Nagase, Takatsuki, all of Japan

[73] Assignee: Sumitomo Chemical Company, Limited, Osaka, Japan

[21] Appl. No.: 840,128

[22] Filed: Oct. 7, 1977

[30] Foreign Application Priority Data

Oct. 12, 1976 [JP] Japan .................................. 51-122403
Oct. 14, 1976 [JP] Japan .................................. 51-123627

[51] Int. Cl.² .................. C07D 307/46; C07D 307/50
[52] U.S. Cl. ............................ 260/347.8; 260/347.9
[58] Field of Search ........................... 260/347.8, 347.9

[56] References Cited

U.S. PATENT DOCUMENTS 4,076,733 2/1978 Dahlgren .......................... 260/347.9

FOREIGN PATENT DOCUMENTS 1024196 3/1953 France.
39699 12/1970 Japan.

OTHER PUBLICATIONS

Katsuda et al., Agr. Biol. Chem., vol. 33, (1969), pp. 1361–1362.
Hurd et al, Journal of the American Chemical Society, vol. 54, (1932), pp. 317–330.
Haworth et al., J. Chem. Soc., (1944), pp. 667–670.

*Primary Examiner*—Richard Raymond
*Attorney, Agent, or Firm*—Stevens, Davis, Miller & Mosher

[57] ABSTRACT

A process for producing furan derivatives of the formula,

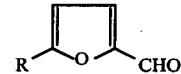

wherein R is hydrogen, methyl or chloromethyl, which comprises reacting a mono- or a disaccharide with hydrochloric acid in a mixture containing water, an organic solvent and a catalytic amount of a surface active agent.

9 Claims, No Drawings

PROCESS FOR PRODUCING A FURAN DERIVATIVE

The present invention relates to an improved process for producing a furan derivative of the formula (I):

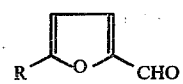
(I)

wherein R is hydrogen, methyl, or chloromethyl, which comprises reacting a monosaccharide or a disaccharide with hydrochloric acid in a mixture containing water, an organic solvent and a catalytic amount of a surface active agent.

The furan derivatives of the formula (I) as above is useful as intermediates for medicines and agricultural chemicals. (e.g., Agr. Biol. Chem., 33, 1361 (1969))

Hitherto, it has been known that furfural derivatives can be prepared by converting a monosaccharide or a disaccharide with acids into corresponding furfural derivatives. For example, furfural can be prepared by reacting a pentose, for example, xylose with conc. sulfuric acid or with conc. hydrochloric acid in a yield of about 30 to 40%. (J. Amer. Soc., 54, 317, 1932)

5-Hydroxymethylfurfural can be obtained by decomposing saccharose in a yield of 30%, using dilute oxalic acid.

Further, 5-chloromethylfurfural is obtained from saccharose in a water-carbon tetrachloride mixed solvent, in a yield of about 21%, using conc. hydrochloric acid. In either case, the yields are low (J. Chem. Soc., 667,1944).

All these techniques can not be applied to commercial scale production, because gelation and resinification which make the operation very troublesome take place in the course of reaction and moreover because the yields are very low.

Furthermore, in the case of production of furfural derivatives by the acid decomposition of saccharose, it is said that only the fructose portion (which structurally belongs to ketohexose) of the saccharose molecule takes part in this reaction, while the glucose portion thereof hardly does under these conditions. In other words, the acid decomposition of glucose structurally belonging to aldohexose has to be carried out after the glucose is pretreated with an alkali such as potassium hydroxide or calcium hydroxide.

In hitherto-known acid decompositions of saccharides, as described above, filtration and separation after the reaction are difficult because of the formation of a large amount of humus produced by the reaction. Therefore, for example, in the commercial production of 5-chlorometylfurfural, there is disclosed a process wherein the acetoxymethyl group of 5-acetoxymethylfurfural is converted to a chloromethyl group by reaction with hydrochloric acid (Japanese Patent Publication No. 39699/1970). This process, however, is not always favorable as a commercial one, because the objective 5-chloromethylfurfural is obtained only through several steps such as acetylation and formylation from furfuryl alcohol.

As the result of an extensive study, the inventors have found that, when the conversion of monosaccharides or disaccharides with hydrochloric acid into furan derivatives is carried out in a mixture containing water, an organic solvent and a catalytic amount of a surface active agent, desired furan derivatives can be prepared in a high yield even if aldohexoses such as glucose is used. Moreover, by using the mixture of the present invention, said drawbacks of hitherto known processes such as formation of humus and resinification after reaction can be overcome and undesired hydrolysis of the product can be prevented with the aid of the formation of a micelle-like state in the reaction mixture. Also, it is of great significance that the commercial production of important intermediates for medicines or agricultural chemicals, which has so far been demanded, is made possible using abundant and cheap saccharides, such as glucose, fructose and saccharose, as raw material, on the basis of the new discovery that saccharides are advantageously decomposed with hydrochloric acid in the mixture of the present invention.

The process of the present invention can generally be applied to pentoses, methylpentoses, ketohexoses, aldohexoses and a disaccharide composed of hexose residues.

Specifically, pentoses (e.g. xylose, ribose, arabinose, etc.,) and methylpentoses (e.g. rhamnose, fucose, etc.,) can be converted to furfural and 5-methylfurfural respectively, and 5-chloromethylfurfural can be prepared from aldohexoses (e.g. glucose, galactose, mannose, etc.,), ketohexoses (e.g. fructose, sorbose, etc.,) and disaccharides (e.g. saccharose, maltose, lactose, etc.).

Thus, the present invention provides a process for producing a furan derivative of the formula (I) as above, which comprises reacting a monosaccharide which may be pentose, methylpentose or hexose or a disaccharide composed of hexose residues with hydrochloric acid in a mixture containing water, an organic solvent and a catalytic amount of a surface active agent.

In practising the process of the present invention, said saccharides are mixed with hydrochloric acid in the presence of an inert organic solvent and a catalytic amount of a surface active agent. The hydrochloric acid may be added in full at the beginning of the reaction or continuously or intermittently with the progress of the reaction, or hydrogen chloride gas may be introduced into an aqueous solution of the saccharide. When an excess amount of hydrogen chloride gas is used, it can be recycled in the above reaction system.

Generally, hydrochloric acid can be used in an amount of 1 to 5 moles, per 1 mole of a saccharide used in the process of the present invention. As the organic solvent used in the reaction, inert organic solvents, for example, aromatic hydrocarbons such as benzene, toluene, xylene, halogen derivatives thereof such as chlorobenzene and aliphatic hydrocarbons and derivatives thereof such as methylene chloride, chloroform and carbon tetrachloride can be employed.

The volume ratio of water/organic solvent varies from ½ to 1/20, preferably from ⅓ to 1/10.

The weight ratio of saccharide/water is usually 1/1–1/5.

The surface active agent used in the present invention includes anionic, cationic and amphoteric ones. Among them, the anionic and amphoteric surface active agents are preferred and the cationic ones are next, when they are used alone. The anionic surface active agents include alkali metal salts of a higher fatty acid (e.g. sodium laurate, sodium palmitate, sodium stearate, sodium oleate), salts of a higher alkyl sulfonic acid (e.g. sodium alkylbenzenesulfonates such as sodium laurylbenzenesulfonate and sodium dodecylbenzenesulfonate), and salts of a higher alcohol sulfonic acid ester (e.g. sodium lauryl sulfate sodium cetyl sulfate, sodium oleyl sulfate). The cationic surface active agents include those of a quaternary ammonium salt type (e.g. tetrabutylammonium chloride, tetrabutylammonium bromide, cetyltrimethylammonium chloride, cetyldimethylbenzylammonium chloride, tetradecyldimethylbenzylammonium chloride, stearyltrimethylammonium chloride, tricaprylmonomethylammonium chloride, lauryldimethylbenzylammonium chloride; pyridinium salts such as cetylpyridinium chloride) and those of an amine salt type. The amphoteric surface active agents include those of an amino acid type (e.g. sodium laurylaminopropionate) and those of a betaine type (e.g. lauryldimethyl betaine, stearyl-dimethyl betaine, laurylhydroxyethyl betaine).

These three kinds of surface active agent may be used alone or in combination. When they are used in combination, such combinations as anionic/amphoteric, cationic/amphoteric and anionic/cationic are used. Preferred combinations among them are anionic/cationic and anionic/amphoteric mixtures, each of which contains both components in approximately the same amounts. In these cases, the system forms a micelle-like state in which the resinification is little and the treatment after reaction is easy. A preferred specific combination is, for example, a mixture of 1 part of a higher alkylsulfonate and 1 part of a quaternary ammonium salt. The amount of surface active agent used is 1/1000 to 1/10 mole, preferably 1/200 to 1/50 mole, based on 1 mole of said saccharide.

The reaction temperature is not particularly limited. Heating is preferred to promote the reaction, but the temperature range of 100° C. or less, preferably from about 10° C. to about 60° C. is suitable to inhibit side reactions. Under these conditions, the reaction generally comes to an end in 1 to 10 hours. The progress of the reaction can be followed up with the aid of gas chromatography or other usual methods. After the reaction is finished, the objective furan derivatives (I) such as 5-chloromethylfurfural are obtained in a high purity from the reaction solution. If necessary, the derivatives obtained may be purified by chromatography or other usual methods.

As described in detail, the commercial production of the furan derivatives (I) becomes very advantageous according to the process of the present invention. For example, in the case of 5-chloromethylfurfural, 5-propargylfurfuryl alcohol derived therefrom produces the pyrethroid compounds which are important as excellent insecticides.

The present invention will be illustrated in more detail with reference to the following examples, which are not however intended to limit the invention thereto.

EXAMPLE 1

To a three-necked flask equipped with a condenser and a stirrer were added 5 g (0.028 mole) of a commercially available D-(−)-fructose and two kinds of surface active agent, i.e., 89.6 mg (0.00028 mole) of cetyltrimethylammonium chloride and 97.6 mg (0.00028 mole) of sodium laurylbenzenesulfonate. Then, 5 ml of water and 30 ml of toluene were added thereto and the mixture was stirred. Thereafter, a molar excess of hydrogen chloride (about 15 g) was passed through the mixture at room temperature for about 40 minutes with thorough stirring. After stirring was continued at room temperature for a further 2.5 hours, the upper toluene layer was separated from the lower aqueous layer. Thirty milli-liters of toluene and the above two surface active agents in the same amounts as above were then freshly added to the aqueous layer. After the mixture was stirred at room temperature for 2.5 hours, the upper toluene layer was again separated. This toluene extraction operation was repeated three times in total. All the toluene layers were combined and filtered through Celite. The filtrate was neutralized with an aqueous sodium hydrogen carbonate solution, dried over anhydrous sodium sulfate and concentrated. Thus, about 3.10 g (theoretical yield 4.01 g) of 5-chloromethylfurfural was obtained as a crude liquor of pale brown color.

EXAMPLE 2

To a three-necked flask equipped with a condenser and a stirrer were added 5 g (0.014 mole) of a commercially available D-(+)-saccharose and two kinds of surface active agent, i.e., 47.1 mg (0.00014 mole) of cetyltrimethylammonium chloride and 51.3 mg (0.00014 mole) of sodium laurylbenzenesulfonate. Then, 5 ml of water and 30 ml of toluene were added thereto and the mixture was stirred. Thereafter, a molar excess of hydrogen chloride was passed through the mixture at room temperature for about 30 minutes with thorough stirring. After the reaction was continued at room temperature for a further 3 hours, the upper toluene layer was separated from the lower aqueous layer. Thirty milli-liters of toluene and the above two surface active agents of the same amounts as above were then freshly added to the aqueous layer. After the reaction was carried out at room temperature for 3 hours, the upper toluene layer was again separated. This toluene extraction operation was repeated three times in total. All the toluene layers were combined and filtered through Celite. The filtrate was neutralized with an aqueous sodium hydrogen carbonate solution, dried over anhydrous sodium sulfate and concentrated. Thus, about 2.6 g of 5-chloromethylfurfural was obtained as a crude product.

EXAMPLE 3

To a three-necked flask equipped with a condenser and a stirrer were added 5 g (0.028 mole) of a commercially available D-(+)-glucose and two kinds of surface active agent, i.e., 97.6 mg (0.00028 mole) of sodium laurylbenzenesulfonate and 89.6 mg (0.00028 mole) of cetyltrimethylammonium chloride. Then, 5 ml of water and 30 ml of toluene were added thereto and the mixture was stirred. Thereafter, a molar excess of hydrogen chloride (about 13 g) was passed through the mixture at room temperature for about 25 minutes with thorough stirring, and then stirring was continued at 45° C. for a further 3 hours. After the supernatant toluene layer was separated from the reaction solution, 30 ml of toluene was freshly added to the residual aqueous layer. After the mixture was stirred at 45° C. for 2 hours, the upper toluene layer was again separated. This toluene extraction operation was repeated four times in total. All the toluene layers were combined and filtered through Celite. The filtrate was neutralized with an aqueous sodium hydrogen carbonate solution, dried over anhydrous sodium sulfate and concentrated. Thus, about 2.4 g (theoretical yield 4.01 g) of 5-chloromethylfurfural was obtained as a crude liquor of pale brown color.

EXAMPLE 4

To the same three-necked flask as in Example 1 were added 5 g (0.028 mole) of a commercially available D-(+)-galactose and two kinds of surface active agent, i.e., 89.6 mg (0.00028 mole) of cetyltrimethylammonium chloride and 97.6 mg (0.00028 mole) of sodium laurylbenzenesulfonate. Then, 30 ml of toluene was added thereto and the mixture was stirred to make a suspension. Thereafter, about 6 ml of 35% aqueous hydrochloric acid was added dropwise from a dropping funnel over about 1 hour. A slight excess of hydrogen chloride was then slowly passed therethrough at 50° C. over 3 hours with stirring. After stirring was continued for a further 5 hours, the reaction solution was diluted with a little water and filtered through Celite while being washed with toluene. The toluene layer was neutralized, dried and concentrated to obtain about 1.9 g (theoretical yield 4.01 g) of 5-chloromethylfurfural as a crude product.

EXAMPLE 5

To the same three-necked flask as in Example 1 were added 5 g (0.028 mole) of a commercially available D-(−)-fructose and two kinds of surface active agent, i.e., 62.2 mg (0.00028 mole) of sodium laurate and 90.2 mg (0.00028 mole) of tetrabutylammonium bromide. Then, 5 ml of water and 30 ml of carbon tetrachloride were added thereto and the mixture was stirred. Thereafter, a molar excess of hydrogen chloride was passed through the mixture at room temperature for about 30 minutes. After stirring was continued at room temperature for a further 2.5 hours, the lower carbon tetrachloride layer was separated from the upper aqueous layer. Thirty milli-liters of carbon tetrachloride and the above two surface active agents of the same amounts as above were then freshly added to the aqueous layer. After stirring was continued at room temperature for 2.5 hours, the lower carbon tetrachloride layer was again separated. This carbon tetrachloride extraction operation was repeated three times in total. All the carbon tetrachloride layers were combined and filtered through Celite. The filtrate was neutralized, dried and concentrated to obtain about 2.0 g of 5-chloromethylfurfural as a crude product.

EXAMPLE 6

To a three-necked flask equipped with a condenser and a stirrer were added 2.5 g (0.014 mole) of a commercially available L-(−)-sorbose and two kinds of surface active agent, i.e., 47.1 mg (0.00014 mole) of cetyltrimethylammonium chloride and 51.3 mg (0.00014 mole) of sodium laurylbenzenesulfonate. Then, 2.5 ml of water and 15 ml of toluene were added thereto and the mixture was stirred. Thereafter, a molar excess of hydrogen chloride was passed through the mixture at room temperature for about 30 minutes, and the mixture was stirred at room temperature for a further 2.5 hours. The reaction solution was filtered through Celite while being washed with a small amount of a water-toluene mixture. The toluene layer was neutralized, dried and concentrated to obtain about 1.0 g (theoretical yield 2.0 g) of 5-chloromethylfurfural as a crude product.

EXAMPLE 7

To a three-necked flask were added 5 g (0.033 mole) of a commercially available D-(+)-xylose and two kinds of surface active agent, i.e., 130 mg (0.00033 mole) of cetyldimethylbenzylammonium chloride and 114 mg (0.00033 mole) of sodium laurylbenzenesulfonate. Then, 30 ml of toluene was added thereto and the mixture was stirred to make a suspension. Thereafter, about 6 ml of 35% aqueous hydrochloric acid was added dropwise from a dropping funnel over about 1 hour with thorough stirring. A slight excess of hydrogen chloride was then slowly passed therethrough at 50° C. over 3 hours with stirring, and then stirring was continued for a further 5 hours. The reaction solution was diluted with a little water and filtered through Celite while being washed with toluene. The toluene layer was neutralized, dried and concentrated to obtain about 1.9 g (theoretical yield 3.17 g) of furfural as a crude product.

EXAMPLE 8

To a three-necked flask equipped with a condenser and a stirrer were added 5 g (0.027 mole) of a commercially available L-(+)-rhamnose hydrate (6-desoxy-L-mannose hydrate) and two kinds of surface active agent, i.e., 86.4 mg (0.00027 mole) of cetyltrimethylammonium chloride and 94.1 mg (0.00027 mole) of sodium laurylbenzenesulfonate. Then, 5 ml of water and 30 ml of toluene were added thereto and the mixture was stirred. Thereafter, a molar excess of hydrogen chloride was passed through the mixture at room temperature for about 35 minutes with thorough stirring. After stirring was continued at 50° C. for a further 3 hours, the upper toluene layer was separated from the lower aqueous layer. Thirty milli-liters of toluene and the above two surface active agents in the same amounts as above were then freshly added to the aqueous layer. After stirring was continued at 50° C. for 3 hours, the upper toluene layer was again separated. This toluene extraction operation was repeated three times in total. All the toluene layers were combined and filtered through Celite. The filtrate was neutralized with sodium hydrogen carbonate, dried over anhydrous sodium sulfate and concentrated. Thus, about 1.8 g (theoretical yield 2.97 g) of 5-methylfurfural was obtained as a crude product.

EXAMPLE 9

To a three-necked flask equipped with a condenser and a stirrer were added 5 g (0.028 mole) of a commercially available D-(−)-fructose and a surface active agent, 82.3 mg (0.00028 mole) of lauryldimethylbetaine. Then, 5 ml of water and 30 ml of toluene were added thereto and the mixture was stirred. Thereafter, a molar excess of hydrogen chloride was passed through the mixture at room temperature for about 30 minutes with thorough stirring. After the reaction was continued at room temperature for a further 3 hours, the upper toluene layer was separated from the lower aqueous layer. Thirty milli-liters of toluene and the above surface active agent in the same amount as above were then freshly added to the aqueous layer. After the reaction was carried out at room temperature for 3 hours, the upper toluene layer was again separated. This toluene extraction operation was repeated three times in total. All the toluene layers were combined and filtered through Celite. The filtrate was neutralized with an aqueous sodium hydrogen carbonate solution, dried over anhydrous sodium sulfate and concentrated. Thus, about 2.9 g of 5-chloromethylfurfural was obtained as a crude product.

EXAMPLE 10

To a three-necked flask equipped with a condenser and a stirrer were added 5 g (0.028 mole) of a commercially available D-glucose and two kinds of surface active agent, i.e., 97.6 mg (0.00028 mole) of sodium laurylbenzenesulfonate and 89.6 mg (0.00028 mole) of cetyltrimethylammonium chloride. Then, 30 ml of toluene was added thereto and the mixture was stirred to make a suspension. Thereafter, about 6 ml of 35% hydrochloric acid was slowly dropwise added from a dropping funnel over 1 hour with stirring. A slight excess of hydrogen chloride was then slowly passed therethrough at 45° C. over 3 hours with stirring. After stirring was continued for a further 4 hours, the reaction solution was diluted with a little water and filtered through Celite while being washed with toluene. The toluene layer was neutralized, dried and concentrated to obtain about 1.9 g of 5-chloromethylfurfural.

EXAMPLE 11

To the same three-necked flask were added 5 g of a commercially available D-glucose and two kinds of surface active agent, i.e., 97.6 mg of sodium laurylbenzenesulfonate and 89.6 mg of cetyltrimethylammonium chloride. Then, 5 ml of water and 30 ml of toluene were added thereto and the mixture was stirred. Thereafter, a molar excess of hydrogen chloride was passed through the mixture at room temperature for 25 minutes. Stirring was continued at 50° C. for a further 7 hours. The reaction solution was diluted with a little water and filtered through Celite while being washed with toluene. The toluene layer was treated in the same manner to obtain about 1.7 g of 5-chloromethylfurfural.

EXAMPLE 12

To the same three-necked flask were added 5 g of a commercially available D-glucose and two kinds of surface active agent, i.e., 97.6 mg of sodium laurylbenzenesulfonate and 89.6 mg of cetyltrimethylammonium chloride. Then, 5 ml of water and 30 ml of carbon tetrachloride were added thereto and the mixture was stirred. Thereafter, a molar excess of hydrogen chloride was passed through the mixture at room temperature for 25 minutes. Stirring was continued at 50° C. for a further 7 hours. The reaction solution which seemed to gel slightly was filtered through Celite while being washed with small amounts of water and carbon tetrachloride. The lower carbon tetrachloride layer was neutralized, dried and concentrated to obtain about 1.5 g of 5-chloromethylfurfural.

EXAMPLE 13

Five grams of a commercially available D-glucose and 97.6 mg of sodium laurylbenzenesulfonate were added to the same three-necked flask. Then, 5 ml of water and 30 ml of toluene were added thereto and the mixture was stirred. Thereafter, a molar excess of hydrogen chloride was passed through the mixture at room temperature for about 25 minutes. Stirring was continued at 50° C. for a further 7 hours. The reaction solution was diluted with a little water and filtered through Celite while being washed with toluene. The upper toluene layer was neutralized, dried and concentrated to obtain about 1.4 g of 5-chloromethylfurfural.

COMPARATIVE EXAMPLE 1

Five grams (0.028 mole) of a commercially available D-glucose was added to a three-necked flask equipped with a condenser and a stirrer, and dissolved in 5 ml of water. Thirty milli-liters of toluene was further added and the mixture was stirred. Thereafter, a molar excess of hydrogen chloride (about 12 g) was passed through the mixture at room temperature for 30 minutes with thorough stirring. Stirring was further continued at 45° C. for 5 hours. The reaction solution containing a small amount of humud was diluted with a little water and filtered through Celite while being washed with a small amount of toluene. The toluene layer was neutralized with an aqueous sodium hydrogen carbonate solution, dried over anhydrous sodium sulfate and concentrated. Thus, about 1.0 g (theoretical yield 4.01 g) of 5-chloromethylfurfural was obtained as a crude product of pale brown color.

What is claimed is:

1. A process for producing a furan derivative of the formula (I):

wherein R is hydrogen, methyl or chloromethyl, which comprises reacting a monosaccharide or a disaccharide with hydrochloric acid in a mixture containing water, an organic solvent and a catalytic amount of a surface active agent, wherein the volume ratio of water to organic solvent is 1:2 to 1:20, wherein said monosaccharide is pentose, methylpentose or hexose, and said disaccharide is composed of hexose residues.

2. A process according to claim 1, wherein said surface active agent is used in an amount of 0.001 to 0.1 mole per 1 mole of the saccharide used.

3. A process according to claim 1, wherein said surface active agent is used in an amount of 0.005 to 0.02 mole per 1 mole of the saccharide used.

4. A process according to claim 1, wherein said surface active agent is anionic, cationic or amphoteric.

5. A process according to claim 1, wherein said surface active agent is sodium laurate, sodium palmitate, sodium stearate, sodium oleate, sodium laurylbenzenesulfonate, sodium dodecylbenzenesulfonate, sodium laurylsulfate, sodium cetylsulfate, sodium oleylsulfate, tetrabutylammonium chloride, tetrabutylammonium bromide, cetyltrimethylammonium chloride, cetyldimethylbenzylammonium chloride, tetradecyldimethylbenzylammonium chloride, stearyltrimethylammonium chloride, tricaprylmonomethylammonium chloride, lauryldimethylbenzylammonium chloride, cetylpyridinium chloride, sodium laurylaminopropionate, lauryldimethyl betaine, stearyldimethyl betaine, laurylhydroxyethyl betaine, or a mixture thereof.

6. A process according to claim 1, wherein said surface active agent is used as the combination of anionic/cationic in approximately the same amounts.

7. A process according to claim 1, wherein said organic solvent is benzene, toluene, xylene, chlorobenzene, methylene chloride, chloroform, carbon tetrachloride or a mixture thereof.

8. A process according to claim 1, wherein said saccharide is xylose, ribose, arabinose, glucose, galactose, mannose, fructose, sorbose, rhamnose, fucose, saccharose, maltose, or lactose.

9. A process for producing a 5-chloromethylfurfural, which comprises reacting a glucose, fructose or saccharose with hydrochloric acid in a mixture containing water, an organic solvent, wherein the volume ratio of water to organic solvent is 1:2 to 1:20, and a catalytic amount of a surface active agent.

* * * * *